United States Patent [19]

Owiti et al.

[11] Patent Number: 5,530,137
[45] Date of Patent: Jun. 25, 1996

[54] METHODS AND COMPOSITIONS FOR STABILIZING FATTY ACID IMIDAZOLINE SOLUTIONS

[75] Inventors: Clarice A. Owiti, Nairobi, Kenya; Abdul Q. Khan, Jacksonville, Fla.

[73] Assignee: Betz PaperChem, Inc., Jacksonville, Fla.

[21] Appl. No.: 307,975

[22] Filed: Sep. 16, 1994

[51] Int. Cl.$^6$ .................. C07D 233/14; C07D 233/22
[52] U.S. Cl. .................. 548/350.1; 252/51.5 A
[58] Field of Search .................. 548/350.1; 252/51.5 A

[56] References Cited

U.S. PATENT DOCUMENTS

| | | | |
|---|---|---|---|
| 2,211,001 | 8/1940 | Chwala | 548/350.1 |
| 2,468,180 | 4/1949 | De Groote et al. | 548/350.1 X |
| 2,669,546 | 2/1954 | Zussman et al. | 548/350.1 X |
| 2,945,821 | 7/1960 | Sterlin | 548/350.1 X |
| 3,006,007 | 10/1962 | Freedman | 44/63 |
| 3,186,912 | 6/1965 | Beamer | 548/350.1 X |
| 3,316,232 | 4/1967 | McGann | 548/350.1 X |
| 3,403,163 | 9/1968 | Fuchsman | 548/350.1 X |
| 4,362,737 | 12/1982 | Schafer et al. | 548/350.1 X |
| 4,536,311 | 8/1985 | Horodysky | 252/51.5 A |

FOREIGN PATENT DOCUMENTS

| | | | |
|---|---|---|---|
| 0604018 | 8/1960 | Canada | 548/350.1 |

*Primary Examiner*—Floyd D. Higel
*Attorney, Agent, or Firm*—Alexander D. Ricci; Philip H. Von Neida

[57] ABSTRACT

Composition and methods for stabilizing aqueous solutions of fatty acid imidazoline compounds. The methods employ the composition of fatty acid imidazoline compound and glycol ether compound, with and without an acid compound, to stabilize the aqueous fatty acid imidazoline solution.

14 Claims, 5 Drawing Sheets

METHODS AND COMPOSITIONS FOR STABILIZING FATTY ACID IMIDAZOLINE SOLUTIONS

FIELD OF THE INVENTION

Disclosed are compositions and methods for preparing stable aqueous solutions of fatty acid imidazoline compounds.

BACKGROUND OF THE INVENTION

Fatty acid imidazoline compounds have many uses. They function as detergents, emulsifiers, corrosion inhibitors, fungicides, antistatic agents, lubricants and as bonding agents in gravel.

Fatty acid imidazoline compounds are the reaction products of carboxylic acids and polyamines. The carboxylic acids are generally fatty acids of $C_8$ to $C_{18}$ chain length and the polyamines are generally ethylene amines. In most cases, they have been obtained by condensation of ethylene diamine/ethylene diamine derivatives with long chain fatty acids.

Fatty acid imidazolines are exemplified by the general structure:

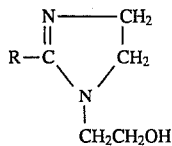

where R is an alkyl hydrophobe radical with a preferred chain length of $C_{12}$ to $C_{18}$, most preferably $C_{16}$ to $C_{18}$. R can be saturated, unsaturated, mono unsaturated or branched alkyl groups.

The fatty acid imidazolines are readily soluble in certain non-polar solvents such as kerosene and mineral oil. These compounds, however, have two inherent shortcomings. They have generally good storage stability except when exposed to moisture. Exposure to water or humid conditions will gradually cause the imidazolines to hydrolyze and either form emulsions, precipitate, gel or separate into more than one phase.

Their other shortcoming is that they are only soluble in organic solvents while remaining relatively insoluble in water. However, their acid salts are water soluble. Neutralization with various common acids such as acetic, hydrochloric, phosphoric or sulfuric acid will make them water soluble. However, the instability in the presence of water remains inherent. Thus, aqueous solutions of fatty acid imidazolines at high concentrations do not remain stable over a long period of time and will decompose or separate into more than one phase. Further, fatty acid imidazoline salts of the water soluble acids tend to swell and form gels at high concentrations.

Oil soluble salts can be formed by neutralization with long chain fatty acids like oleic acid and tall oil, as well as, sulphonates such as L.A.S., linear alkylbenzene sulphonates. Consequently, the solubility characteristics of the fatty acid imidazolines can be altered to suit a wide variety of systems and applications.

The acid used for stabilization will also vary the stability of the resulting solution. Temperature increases will also cause a decrease in stability of the solution. Better stabilities can be achieved if some of the water is replaced with n-hexanol, n-octanol and isopropanol. Still instability problems will exist with this method, particularly at 40° F.

SUMMARY OF THE INVENTION

Figure 1:
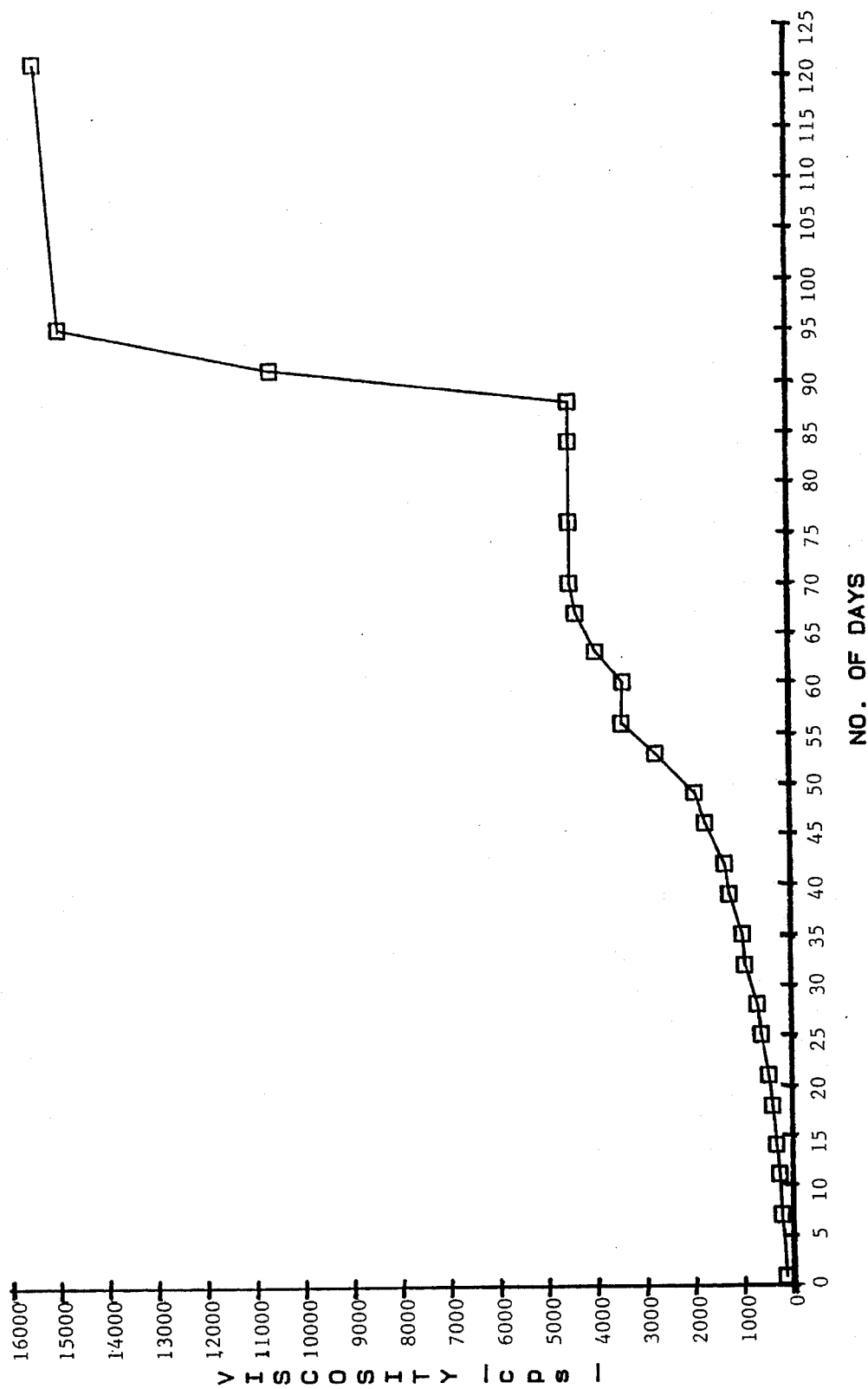
FIG. 1 represents the viscosity profile of a 25.5% fatty acid imidazoline with 7.0% citric acid in water solution at room temperature versus time over 17 weeks.

The present invention provides for compositions and methods for stabilizing aqueous solutions of fatty acid imidazoline compounds. Stabilization is achieved by using glycol ethers alone or with the common acids previously utilized. These solutions will in turn remain relatively stable over a long period of time without gelling or separating into more than one phase. Typical of the imidazoline compounds stabilized is 1-hydroxyethyl, 2-alkylimidazoline.

DESCRIPTION OF THE RELATED ART

U.S. Pat. No. 3,060,007 teaches a rust inhibited hydrocarbon composition comprising a liquid hydrocarbon and the reaction product of a 1,2-disubstituted imidazoline and a substituted alkylene iminodiacetic acid.

DETAILED DESCRIPTION OF THE INVENTION

Disclosed are compositions and methods for stabilizing aqueous solutions of fatty acid imidazoline compounds comprising adding an effective amount of a glycol ether compound to said aqueous solution.

The fatty acid imidazoline compounds generally are $C_{12}$ to $C_{18}$ fatty acid imidazolines. Preferably, these compounds are $C_{16}$ to $C_{18}$ fatty acid imidazolines such as 1-hydroxyethyl, 2-alkylimidazoline utilized in the examples. The fatty acid imidazoline solution may also contain a mixture of two or more fatty acid imidazoline compounds, The glycol ether compounds useful in the present invention have the following formulas:

(I) $CH_3O[CH_2CH(CH_3)O]_nH$ n is 1 to 3

(II) $C_4H_9O(C_2H_4O)_nH$ n is 1 to 2

(III) $C_2H_5O(C_2H_4O)_nH$ n is 1 to 2

(IV) $C_4H_9O(C_3H_6O)_nH$ n is 1 to 2

Preferred glycol ether compounds include diethylene glycol monobutyl ether, dipropylene glycol monomethyl ether, tripropylene glycol monomethyl ether, propylene glycol monomethyl ether and diethylene glycol monoethyl ether. All of these compounds are available commercially from Dow Chemical Corp and Arco Chemical Company.

The glycol ether compounds are preferably used with an acid. The acid is first added to solubilize the fatty acid imidazoline in the aqueous solution. Preferred acids include phosphoric, citric, sulphuric, hydrochloric, gluconic, acetic, propionic and glutaric acids. Most preferred is citric acid.

The acid salt solutions are temperature dependent and stability decreases as temperature increases from 40° F. to room temperature to 122° F. The stability of the acid salt solutions are also dependent on the amount of acid used. Generally, the most favorable amount of acid added is that which will neutralize the fatty acid imidazoline solution. The stability is also affected by the amount of fatty acid imidazoline compound present, with higher levels of imidazoline compounds more prone to gel.

Thus, the amounts of acid and fatty acid imidazoline compounds are both important in the original acid salt solution and the ratio of fatty acid imidazoline compound to acid can be critical and can vary depending upon the type of acid used and the amount of imidazoline utilized and also the desired pH of the end use mixture. The preferred ratio as embodied in the present invention is 3.64 parts fatty acid imidazoline compound to 1.0 parts citric acid. The addition of the glycol ether compounds will lend further stability to this mixture.

When all three components are utilized in the aqueous solution, three steps are utilized to create the stable fatty acid imidazoline solution. First, the imidazoline-water dispersion is created with sufficient stirring to aid in subsequent solubilization.

Second, is to add the acid in the desired amount as previously described. Lastly, the selected glycol ether is added to the solution in amounts ranging from about 3% to about 24.0% depending on the amount of fatty acid imidazoline in solution, pH of the solution and stability desired.

The same stabilization can be achieved using only the glycol ether compounds and the fatty acid imidazoline solution. This generally requires a higher amount of glycol ether compounds than when the acid is present.

The glycol ether compounds, whether employed in a two component system or three component system, can be added to the fatty acid imidazoline solution either neat or as a solution in a suitable carrier solvent. In this invention, the preferred solvent is water.

In order to more clearly illustrate this invention, the data set forth below was developed. The following examples are included as being illustrative of the invention and should not be construed as limiting the scope thereof.

EXAMPLES

Solution viscosities were used as an indication of the swelling and gelling phenomena. This phenomena was therefore measured by monitoring the viscosities of the test solution over a period of 12 weeks. Visual observations were used to determine the stability of the solutions at the various test temperatures.

Example 1

Figure 2:
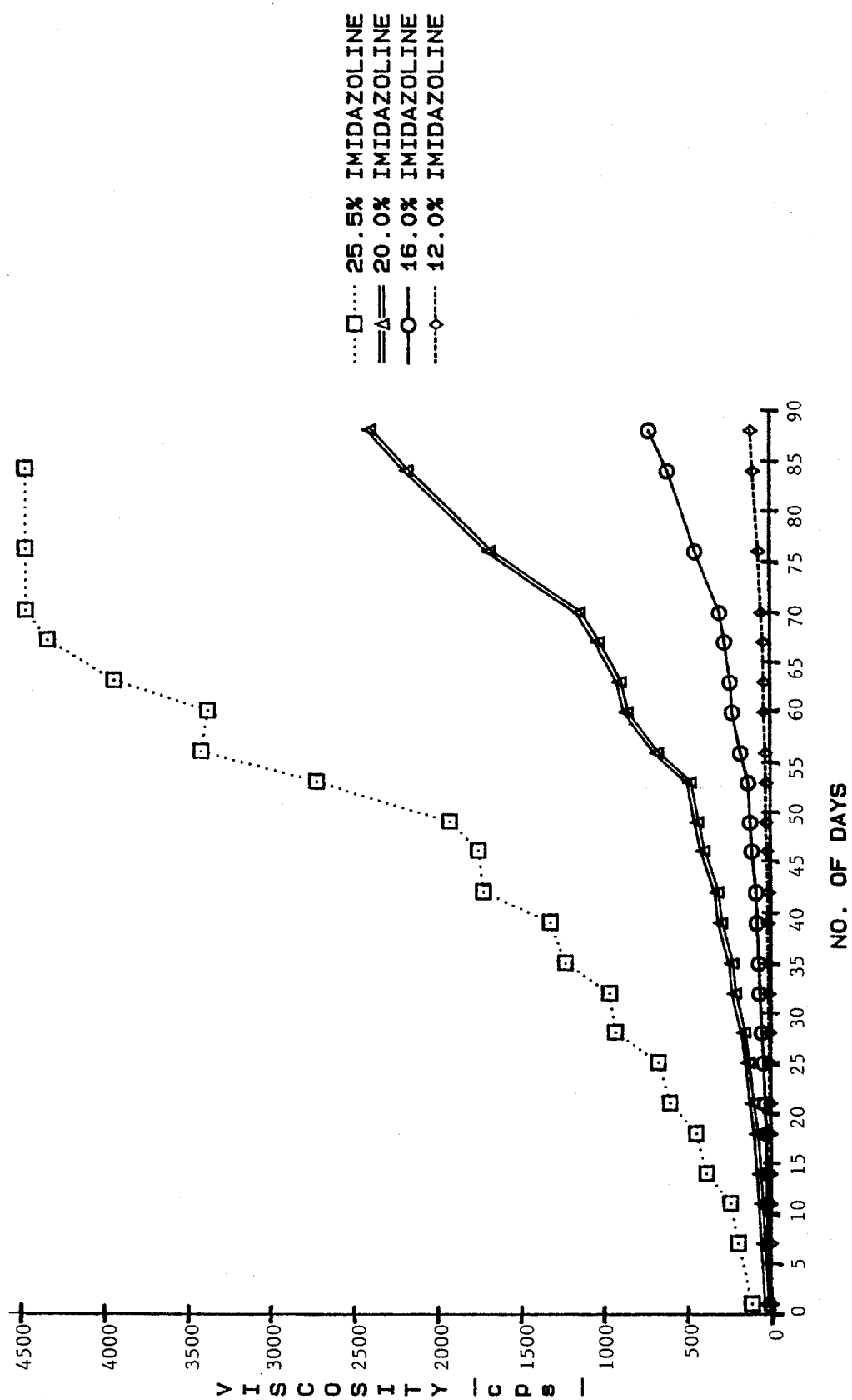
FIG. 2 represents the viscosities of varying fatty acid imidazoline concentrations with 7.0% citric acid in water solution at room temperature versus time over 12 weeks.

To illustrate the acid salt stability dependency on the amount of fatty acid imidazoline, test solution with different amounts of imidazoline in solution (while maintaining the fatty acid imidazoline/acid ratio) were tested. FIGS. 1 and 2 indicate the more fatty acid imidazoline, the more the gelling. All of these solutions separated at room temperature and precipitated at 122° F. within several days.

Example 2

Figure 3:
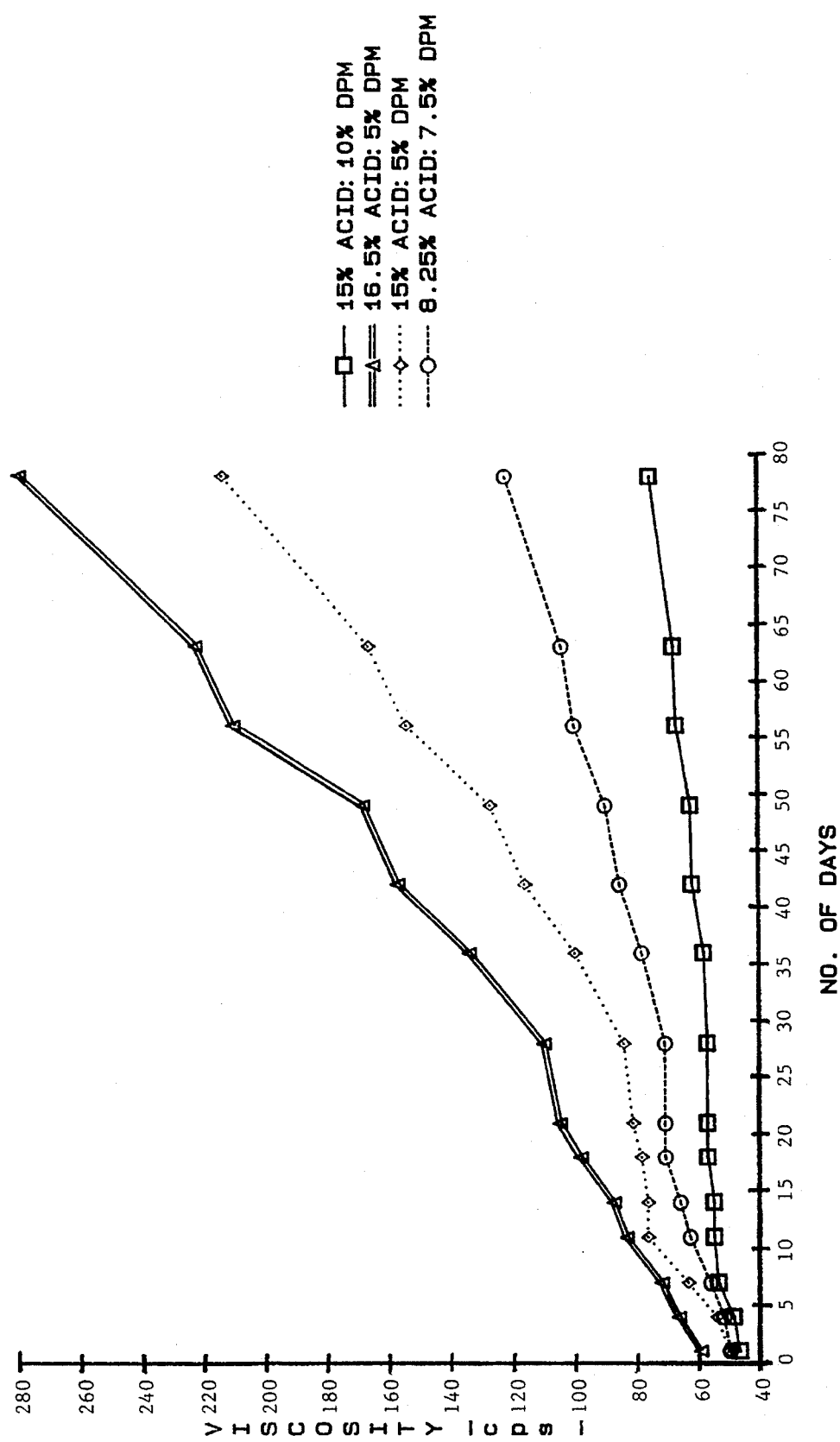
FIG. 3 represents the viscosity of 30% fatty acid imidazoline with varying concentrations of citric acid (8.25–16.5%) and Dowanol® DPM (5–10%) versus time. Dowanol® DPM is dipropylene glycol monomethyl ether.
Figure 4:
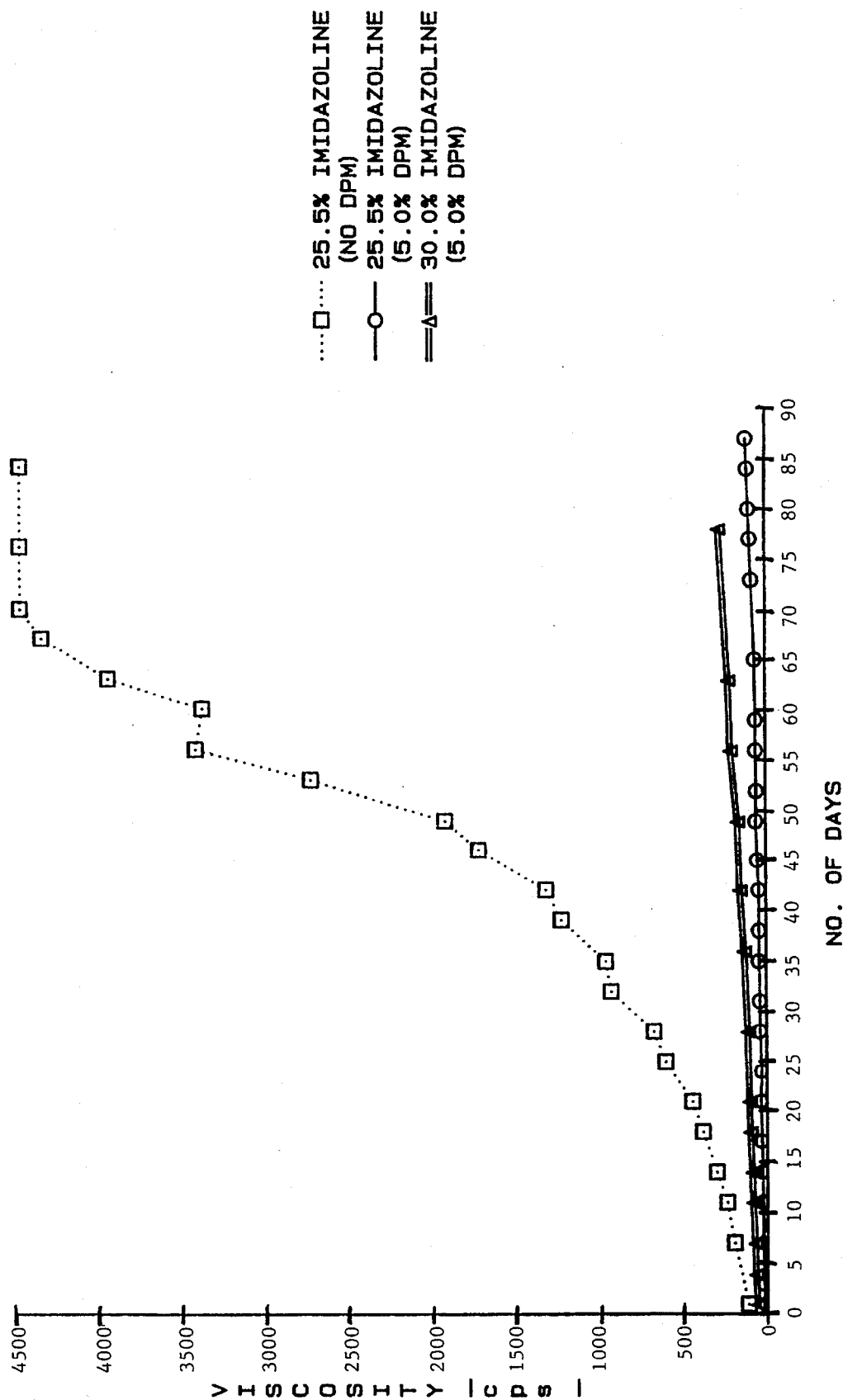
FIG. 4 represents the viscosities of low and high concentration fatty acid imidazoline solutions with and without Dowanol® DPM without any citric acid being present.

FIGS. 3 and 4 illustrate the ability, with glycol ethers, to use high concentrations of fatty acid imidazolines.

Example 3

Figure 5:
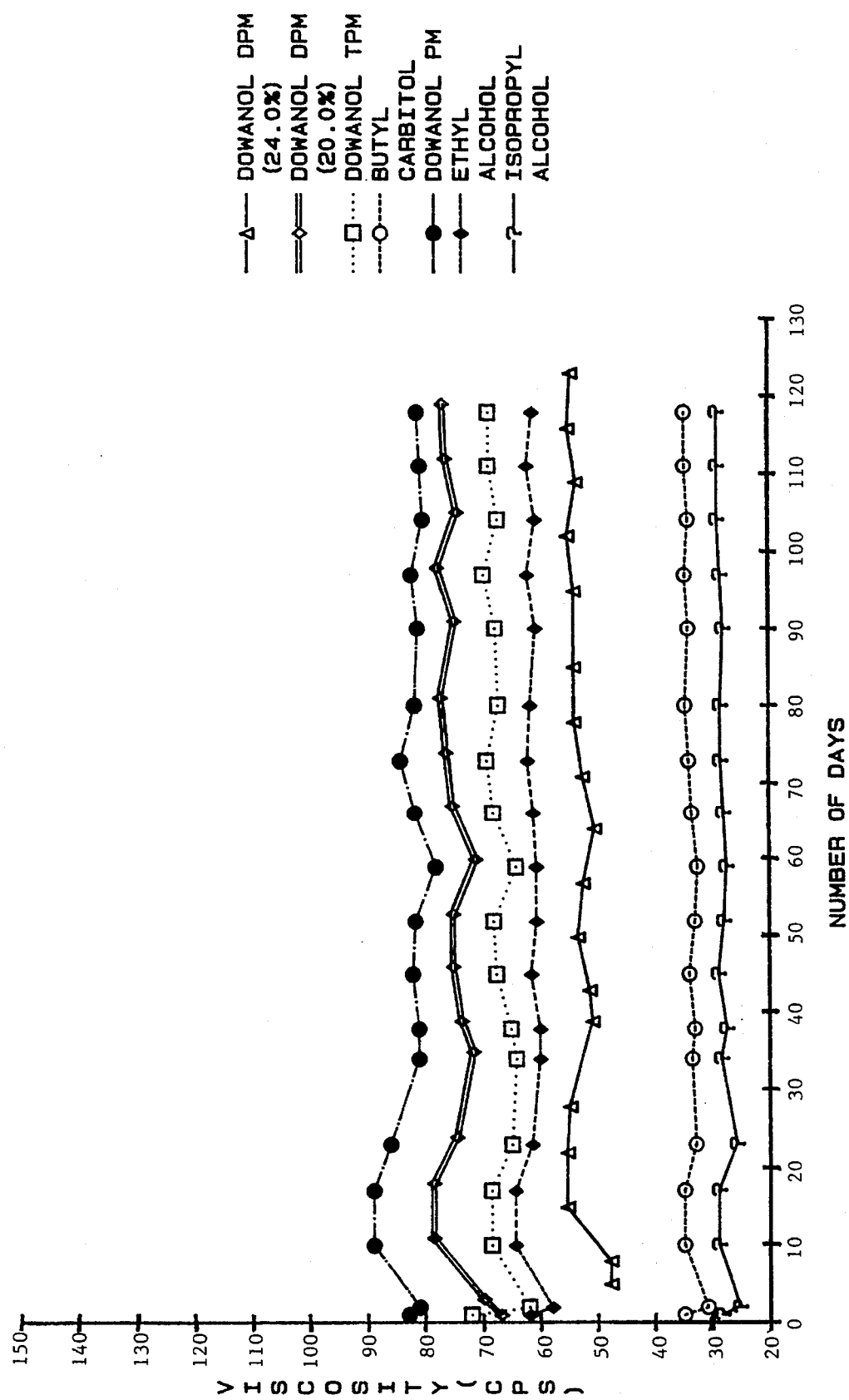
FIG. 5 represents the viscosity of fatty acid imidazoline in various solvents versus time without any citric acid being present.

FIG. 5 represents the same glycol ethers employed without acid in the imidazoline solutions. Similar results were obtained, but higher solvent concentrations (20 to 24% versus 3–5%) were necessary.

Example 4

Table I represents the impact on stability by the glycol ether compounds. At 40° F., the glycol ethers extend the stability much longer than isopropanol.

Table II demonstrates that the glycol ether compounds not only extend the stability period at 40° F., but their solutions become clear much faster than isopropanol when no acid is present.

TABLE I

| Solvent | Initial Room Temp. | 20 Weeks Room Temp. | 40° F. |
|---|---|---|---|
| Dowanol ® TPM[1] | OK | OK | SEP |
| Dowanol ® DPM[1] | OK | OK | OK |
| Dowanol ® PM[1] | OK | OK | SEP |
| Dowanol ® Pnb[1] | OK | OK | OK |
| Dowanol ® DPnb[1] | OK | OK | OK |
| Butyl CelloSolve ®[2] | OK | OK | OK |
| Butyl Carbitol ®[2] | OK | OK | OK |
| Isopropanol | OK | OK | SEP |
| Diethylene glycol monomethyl ether | OK | OK | OK |

[1]available from Dow Chemical
[2]available from Union Carbide Chemicals and Plastics Co.

TABLE II

Stability Results
25.5% Imidazoline
20% Solvent

| Solvent | Initial Room Temp. | 24 Hrs. Room Temp. | 3 Wks. Room Temp. | 40° F. | 17 Wks. Room Temp. | 40° F. |
|---|---|---|---|---|---|---|
| A | Turbid, cleared in 3 hrs. | OK | OK | SEP | OK | Ppt |
| B | Turbid, cleared in 5 hrs. | OK | OK | OK | OK | Ppt |
| C | Turbid, cleared in 3 hrs. | OK | OK | OK | OK | OK |
| D | OK, cleared in 5 min. | OK | OK | OK | OK | OK |
| E | Turbid, cleared in 3 hrs. | OK | OK | SEP | OK | OK |
| F | Emulsified & Separated | Cleared | OK | SEP | OK | — |

TABLE II-continued

| | | Stability Results 25.5% Imidazoline 20% Solvent | | | | |
|---|---|---|---|---|---|---|
| | | 24 Hrs. Room | 3 Wks. Room | | 17 Wks. Room | |
| Solvent | Initial Room Temp. | Temp. | Temp. | 40° F. | Temp. | 40° F. |

A Dowanol ® TPM
B Dowanol ® DPM
C Dowanol ® PM
D Butyl Carbitol ®
E Ethyl Alcohol
F Isopropanol
Ppt = precipitated
SEP = separated While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A stable composition consisting essentially of an aqueous fatty acid imidazoline compound solution, a glycol ether compound selected from the group consisting of diethylene glycol monobutyl ether, dipropylene glycol monomethyl ether, tripropylene glycol methyl ether, propylene glycol monomethyl ether and diethylene glycol monoethyl ether, and water.

2. The composition as claimed in claim 1 wherein said fatty acid imidazoline compound is a $C_{12}$ to $C_{18}$ fatty acid imidazoline.

3. The composition as claimed in claim 1 wherein said fatty acid imidazoline compound is a $C_{16}$ to $C_{18}$ fatty acid imidazoline.

4. The composition as claimed in claim 1 wherein said imidazoline compound is 1-hydroxyethyl, 2-alkylimidazoline.

5. The composition as claimed in claim 1 wherein said fatty acid imidazoline compound solution contains two or more fatty acid imidazoline compounds.

6. The composition as claimed in claim 1 wherein said composition also comprises an acid compound.

7. The composition as claimed in claim 6 wherein said acid compound is selected from the group consisting of phosphoric acid, citric acid, sulphuric acid, hydrochloric acid, gluconic acid, acetic acid, propionic acid and glutaric acid.

8. A method for stabilizing aqueous solutions of fatty acid imidazoline compounds consisting essentially of adding an effective stabilizing amount of a glycol ether compound selected from the group consisting of diethylene glycol monobutyl ether, dipropylene glycol monomethyl ether, tripropylene glycol methyl ether, propylene glycol monomethyl ether and diethylene glycol monoethyl ether to said aqueous solution.

9. The method as claimed in claim 8 wherein said fatty acid imidazoline compound is a $C_{12}$ to $C_{18}$ fatty acid imidazoline.

10. The method as claimed in claim 8 wherein said fatty acid imidazoline compound is a $C_{16}$ to $C_{18}$ fatty acid imidazoline.

11. The method as claimed in claim 8 wherein said fatty acid imidazoline compound solution contains two or more fatty acid imidazolines.

12. The method as claimed in claim 8 wherein said imidazoline compound is 1-hydroxyethyl, 2-alkylimidazoline.

13. The method as claimed in claim 7 wherein said aqueous solution also comprises an acid compound.

14. The method as claimed in claim 13 wherein said acid compound is selected from the group consisting of phosphoric acid, citric acid, sulphuric acid, hydrochloric acid, glutonic acid, acetic acid, propionic acid and glutaric acid.

* * * * *